United States Patent [19]

Satula

[11] Patent Number: 5,233,408
[45] Date of Patent: Aug. 3, 1993

[54] COLOR SENSOR ADAPTOR BRACKET FOR MEASURING FLEXIBLE TRANSLUCENT MATERIALS

[75] Inventor: Keith O. Satula, New Berlin, Wis.

[73] Assignee: Eaton Corporation, Cleveland, Ohio

[21] Appl. No.: 825,901

[22] Filed: Jan. 27, 1992

[51] Int. Cl.⁵ ............................................. G01J 3/50
[52] U.S. Cl. .................................. 356/402; 250/226; 356/429
[58] Field of Search ............... 356/402, 405, 406, 407, 356/425, 429, 430; 250/226

[56] References Cited

U.S. PATENT DOCUMENTS

| | | | |
|---|---|---|---|
| 3,641,626 | 2/1971 | McGill | 356/402 |
| 3,814,932 | 6/1974 | Anati et al. | 356/406 |
| 3,999,860 | 12/1976 | Demsky et al. | 356/402 |
| 4,533,245 | 8/1985 | Love, III | 356/430 |
| 4,618,257 | 10/1986 | Bayne et al. | 356/402 |
| 5,047,652 | 9/1991 | Lisnyansky et al. | 356/429 |

Primary Examiner—F. L. Evans
Attorney, Agent, or Firm—L. H. Uthoff, Jr.

[57] ABSTRACT

An adaptor bracket for the mounting of a color sensor head and a support pad held in a specific orientation such that the light emitted from the color sensor head strikes the support pad in a manner that the reflected light is directed back towards the color sensor head while the support pad serves as a low friction surface over which a flexible translucent material can be passed for measurement of its color quality.

12 Claims, 2 Drawing Sheets

COLOR SENSOR ADAPTOR BRACKET FOR MEASURING FLEXIBLE TRANSLUCENT MATERIALS

FIELD OF THE INVENTION

This invention relates to color measurement of a flexible translucent material. More specifically, this invention relates to an adaptor bracket that is used to mount a color sensor head whose light output is directed towards the flexible material; whose color is to be measured riding on a support pad mounted to the adaptor such that the transmitted light from the color sensor is reflected back by the support pad into a receiving section of the color sensor head.

DESCRIPTION OF THE PRIOR ART

The color of a flexible film-like material such as that used for packaging purposes in the food industry, has traditionally been measured by using some type of color sensor directed toward the surface of the material as it is carried and moved across a plurality of support elements having no specific optical characteristics. The light emitted by the color sensor is not reflected in a predictable manner due to a nonuniform distance and orientation of the material in respect to the sensor making calibration and accurate detection of the color of the flexible material difficult. In the manufacturing process, the flexible material would be supported at points at some distance apart and the tension of the flexible material would vary causing a variation in distance from the surface of the material to the sensor providing for measurement inaccuracy. Also, the surface to color sensor distance would vary as the flexible material passed under the sensor head, creating additional measurement inaccuracy.

SUMMARY OF THE INVENTION

The color sensor adaptor bracket of the present invention allows the flexible material whose color is to be measured to be passed over a low friction support pad whose high reflectivity works with the color sensor to reflect an emitted light from the color sensor head which passes through the flexible material back through the material into the receiving element of the color sensor head. In this manner, the distance between the color sensor head and the flexible material remains relatively constant thereby providing for increased accuracy of a color measurement. The support pad also functions to flatten the material at the point of measurement so that stray light reflection is minimized.

Also, the white color of the low friction support pad provides for a high degree of reflectivity increasing the amount of light that is reflected back into the color sensor receiving means providing for increased signal to noise ratio and more accurate measurement. In addition, the adaptor bracket itself shields the support pad from the ambient light thereby improving the sensor performance especially its signal to noise ratio.

One provision of the present invention is to provide for support of a flexible translucent material whose color is to be measured.

Another provision of the present invention is to provide for a stable mounting of a color sensor in relation to the surface of a flexible material whose color is to be measured.

Another provision of the present invention is to provide a low friction high reflectivity support pad over which a flexible material can be passed for measurement of color in a manufacturing environment.

Another provision of the present invention is to mount a color sensor in a low friction support pad to shield against stray light entry during measurement of color.

Still another provision of the present invention is to provide a low friction support pad for a flexible transparent material which flattens the surface at the point of contact and thereby reduces unwanted irregular light reflections.

DESCRIPTION OF THE PREFERRED EMBODIMENT

Figure 1:
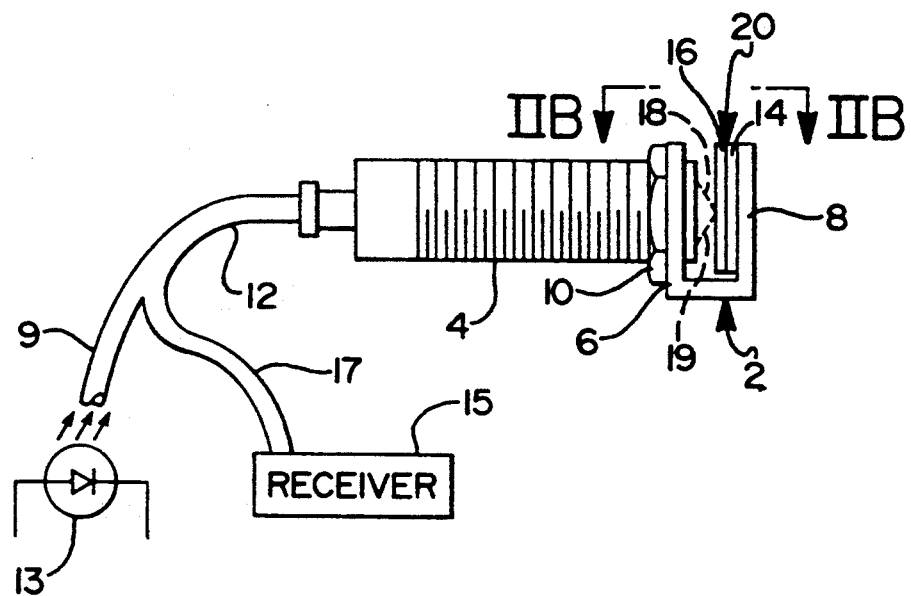
FIG. 1 is a cross-sectional view of a color sensor head mounted to the adaptor bracket of the present invention.

Referring to FIG. 1, a color sensor head 4 is shown mounted to an adaptor bracket 2 where a securing nut 10 is used to secure the color sensor head 4 which is threaded into a sensor support flange 6. The color sensor head 4 can be of a type described more fully in patent application U.S. Ser. No. 07/727,730 titled "Color Sensor Employing Optical Fiber Bundles With Varied Diameters" assigned to the same assignee, Eaton Corporation, as this Application and filed on Jul. 10, 1991, the disclosure of which is hereby expressly incorporated by reference. The color sensor head 4 can incorporate various other means of generating an emitted light 18 which is directed toward a support pad 20. The support pad 20 is mounted to the adaptor bracket 2 on a support pad flange 8 which is connected to a sensor support flange 6 by way of a flange connector 22. Typically, the sensor support flange 6, the support pad flange 8 and the flange connector 22 which combine to make up the adaptor bracket 2 are made of aluminum, although a plastic material could be utilized. In FIG. 1, the adaptor bracket 22 is shaped from a side view in the form of a "u" so that a flexible translucent material can pass between the sensor support flange 6 and the support pad flange 8.

The input and output electrical signals or the optical fibers to the color sensor head 4 are carried on the sensor cable 12 which leads to an electrical processing unit (15) which functions to provide or power the emitting light sources which can be light emitting diodes (13) where only one is shown and also receives the reflected light from the support pad 20 and conducts this light through optical fiber cables (12, 17) to a receiving light sensitive diode (not shown) which can be of PIN type whereupon a microprocessor as part of the processing unit (15) is used to interpret the signals therefrom and output a signal which indicates the color of the reflected light 19.

Figure 2A:
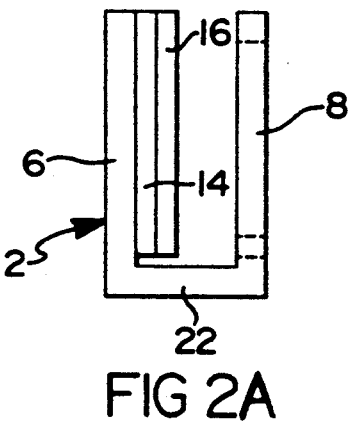
FIGS. 2A and 2B are side, top, and end views of the adaptor bracket of the present invention showing the beveled support pad.
Figure 2B:
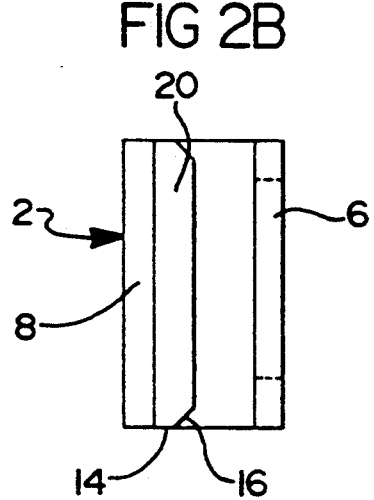

Now referring to FIGS. 2A and 2B, two different views are shown of the adaptor bracket 2 where 2A shows a view similar to that shown in FIG. 1 where the support pad 20 is mounted to the sensor support flange 6 where the support pad 20 has a support pad flat 14 and a support pad bevel 16. The support pad bevel 16 functions to reduce any tendency of the flexible translucent material when passed over the support pad 20 to catch, thereby impeding progress or causing surface damage. The support pad 20 can be made out of a low friction type material such as a synthetic fluorine such as polytetrafluoroethylene commonly known as PTFE, one example being that sold under the tradename of Teflon ® by E. I. duPont de Nemours and Company of Wilmington, Del. or other materials showing a similar low friction characteristic when a flexible translucent material is passed over its surface. Another desirable quality of the support pad 20 is to have a high index of reflectivity relative to the light generated by the color sensor head 4 and shown as emitted light 18 in FIG. 1. The color of the support pad 20 of the present invention is a white color which provides for a high level of reflectivity for generalized color measurement.

FIG. 2B shows the top view of the adaptor bracket 2 showing the support pad bevel 16 and the support pad flat 14. The support pad 20 is bonded or mechanically secured to the support pad flange 8 and the direction of travel of the material whose color is to be measured is such that the axis of travel is perpendicular to the edge line on the top surface of the support pad 20 formed by the support pad bevel 16.

Figure 3:
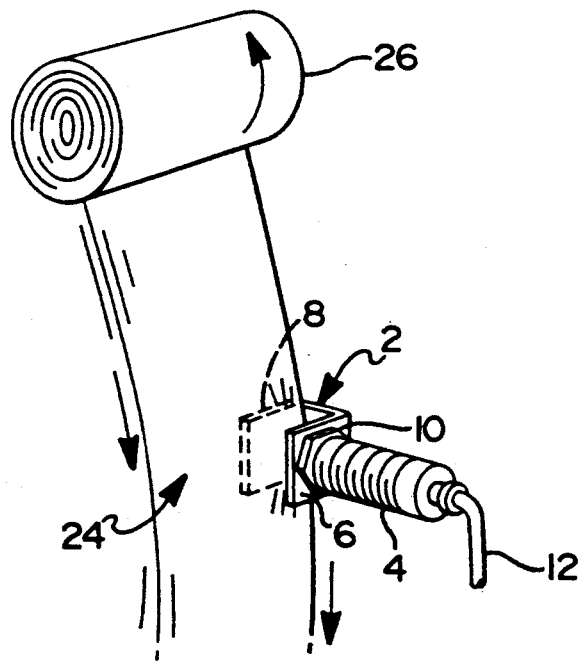
FIG. 3 is a perspective view of a roll of flexible translucent material whose color is being measured with a color sensor mounted to the adaptor bracket of the present invention.

FIG. 3 shows the adaptor bracket 2 with a color sensor head 4 mounted to the sensor support flange 6 by threading into the sensor support flange 6 and retained thereto by securing nut 10. The sensor cable 12 is connected to a signal processing unit (15) which is shown in FIG. 1. A material roll 26 which consists of a length of a flexible translucent material 24 whose color is to be measured where the flexible translucent material 24 is passed between the sensor support flange 6 and the support pad flange 8 (which is shown as a hidden line) so that the emitted light 18 from the color sensor head 4 passes through the flexible translucent material 24 and onto the support pad 20 and is reflected therefrom back through the flexible translucent material 24 and into the color sensor head 4 which contains a light receiving element whose output is then directed along the sensor cables 12 and 17 (which can contain fiberoptic cables) into the signal processing unit. In this manner, the flexible translucent material 24 rubs against and is supported by the support pad 20 which has a low friction characteristic. The support pad 20 flattens the material out at the point of contact thereby reducing any unwanted irregular light reflections and providing for a much more accurate measurement of color. Also, the sensor support flange 6 shields unwanted stray ambient light from entering and being reflected from the support pad 20 improving the accuracy of the color measurement.

It will be appreciated by those of ordinary skill in the art that many variations in the foregoing preferred embodiment are possible while remaining within the scope of the present invention. The present invention should thus not be considered limited in the preferred embodiments or the specific choices of material, configurations, dimensions, applications or ranges of parameter employed therein.

What is claimed is:

1. A color sensor assembly for mounting a color sensor head and for supporting a translating flexible translucent material whose color is to be measured comprising:

a color sensor head having a light emitting means for generating an emitted light and a receiving means for detecting a reflected light;

a support pad having a first side contacting and supporting said translating flexible translucent material, said first side having a relatively low coefficient of friction when said translating flexible translucent material passes thereover and having a high value of reflectivity to said emitted light, said support pad having a second side for mounting;

an adaptor bracket having a first flange connected to a second flange where said support pad second side is mounted to said first flange and where said color sensor head is mounted to said second flange such that said emitted light is directed toward said support pad reflecting therefrom to said receiving means with said translating flexible translucent material interposed between said emitted light and said support pad.

2. The color sensor assembly of claim 1, wherein said adaptor bracket first flange opposes and is parallel to said second flange.

3. The color sensor assembly of claim 1, wherein said support pad is made of a polytetrafluoroethylene material.

4. The color sensor assembly of claim 1, wherein said support pad is white in color.

5. The color sensor assembly of claim 1, wherein said color sensor head contains a randomized bundle of optical fibers.

6. The color sensor assembly of claim 1, wherein said first flange is fixed relative to said second flange.

7. The color sensor assembly of claim 1, wherein said support pad first side is perpendicular to a major axis of said emitted light.

8. The color sensor assembly of claim 1, wherein said light emitting means is a light emitting diode.

9. A method of detecting the color of a translating translucent flexible material comprising:

providing a color sensing means having a light emitting means for generating and directing an emitted light and a receiving means for detecting a reflected light and a processing means for generating a signal indicative of color based on said reflected light;

providing a support pad having a first side contacting and supporting said translating translucent flexible material, said first side having a low coefficient of friction when said translating flexible material passes thereover, said support pad having a high value of reflectivity to said emitted light and said support pad having a second side for mounting;

providing an adaptor bracket having a first flange for mounting said light emitting means and said light receiving means, said adaptor bracket having a second flange for mounting said support pad oriented such that said translating translucent flexible material is interposed between said light emitting means, said receiving means and said support pad;

emitting a light from said light emitting means to pass through said translating translucent flexible material and to impinge upon said support pad;

reflecting said light back through said translating translucent flexible material;

receiving said reflected light with said receiving means;

processing an output of said receiving means to generate a signal indicative of the color of said translating translucent flexible material.

10. The method of detecting the color of the translating translucent flexible material of claim 9, wherein said light emitting means consists of at least one LED projecting light into an optical fiber cable.

11. The method of detecting the color of a translating translucent flexible material of claim 9, wherein said receiving means consists of an optical fiber cable to direct said reflected light to a light sensitive diode.

12. The method of detecting the color of a translating translucent flexible material of claim 9, further comprising:

passing said material over said support pad in a continuous manner.

* * * * *